United States Patent [19]

DeLuca et al.

[11] Patent Number: 5,384,313
[45] Date of Patent: Jan. 24, 1995

[54] 21-NORVITAMIN D COMPOUNDS

[75] Inventors: Hector F. DeLuca, Deerfield, Wis.; Jerzy Wicha, Warsaw, Poland

[73] Assignee: Wisconsin Alumni Research Foundation, Madison, Wis.

[21] Appl. No.: 157,888

[22] Filed: Nov. 24, 1993

[51] Int. Cl.⁶ ............................................. C07C 401/00
[52] U.S. Cl. ..................................... 514/167; 552/653
[58] Field of Search ........................... 552/653; 514/167

[56] References Cited

U.S. PATENT DOCUMENTS 4,711,881 12/1987 Ikekawa ............................... 514/167

OTHER PUBLICATIONS

"Synthetic Studies of Vitamin D Analogues. X. Synthesis and Biological Activities of 1α,25-Dihydroxy-2-1-norvitamin $D_3$", Chem. Pharm. Bull., Kubodera et al. vol. 40, No. 3, pp. 648-651.

Primary Examiner—Johann Richter
Assistant Examiner—Kimberly J. Kestler
Attorney, Agent, or Firm—Andrus, Sceales, Starke & Sawall

[57] ABSTRACT

21-norvitamin $D_3$ analogs in which the methyl group normally attached to the side chain at carbon 20 has been replaced by a hydrogen atom. The compounds are characterized by a marked intestinal calcium transport activity while exhibiting much lower activity than 1α,25-dihydroxyvitamin $D_3$ in their ability to mobilize calcium from bone. Because of their preferential calcemic activity, these compounds are useful for the treatment of diseases where bone formation is desired, such as osteodystrophy. Novel intermediates formed during the synthesis of the end products are also disclosed.

5 Claims, No Drawings

21-NORVITAMIN D COMPOUNDS

This invention was made with United States Government support awarded by the National Institutes of Health (NIH), Grant No. DK-14881. The United States Government has certain rights in this invention.

BACKGROUND OF THE INVENTION

This invention relates to biologically active vitamin D compounds. More specifically, the invention relates to 21-norvitamin D compounds, to a general process for their preparation, and to their use in treating osteoporosis.

With the discovery of $1\alpha,25$-dihydroxyvitamin $D_3$ as the active form of the vitamin has come an intense investigation of analogs of this hormonal form of vitamin D with the intent of finding analogs that have selective activity. By now, several compounds have been discovered which carry out the differentiative role of 1,25-dihydroxyvitamin $D_2$ while having little or no calcium activity. Additionally, other compounds have been found that have minimal activities in the mobilization of calcium from bone while having significant activities in stimulating intestinal calcium transport. Modification of the vitamin D side chain by lengthening it at the 24-carbon has resulted in loss of calcium activity and either an enhancement or undisturbed differentiative activity. Placing the 24-methyl of $1\alpha,25$-dihydroxyvitamin $D_2$ in the epi-configuration appears to diminish activity in the mobilization of calcium from bone. On the other hand, increased hydrophobicity on the 26—and 27—carbons seems to increase the total activity of the vitamin D compounds provided the 25-hydroxyl is present.

Several of these known compounds exhibit highly potent activity in vivo or in vitro, and possess advantageous activity profiles and thus are in use, or have been proposed for use, in the treatment of a variety of diseases such as renal osteodystrophy, vitamin D-resistant rickets, osteoporosis. psoriasis, and certain malignancies.

It is well known that females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the life-span of females reaches ages of at least 60 and 70 years. Generally, the disease which is often accompanied by bone pain and decreased physical activity, is diagnosed by one or two vertebral crush fractures with evidence of diminished bone mass. It is known that this disease is accompanied by diminished ability to absorb calcium, decreased levels of sex hormones, especially estrogen and androgen, and a negative calcium balance.

Similar symptoms of bone loss characterize senile osteoporosis and steroid-induced osteoporosis, the latter being a recognized result of long term glucocorticoid (cortico-steroid) therapy for certain disease states.

Methods for treating the disease have varied considerably but to date no totally satisfactory treatment is yet known. A conventional treatment is to administer a calcium supplement to the patient. However, calcium supplementation by itself has not been successful in preventing or curing the disease. Another conventional treatment is the injection of sex hormones, especially estrogen, which has been reported to be effective in preventing the rapid loss of bone mass experienced in postmenopausal women. This technique, however, has been complicated by the fact of its possible carcinogenicity. Other treatments for which variable results have been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large amounts of fluoride administered. Another suggested method is to block bone resorption by injecting calcitonin or providing phosphonates.

U.S. Pat. No. 4,225,596 suggests the use of various metabolites of vitamin $D_3$ for increasing calcium absorption and retention within the body of mammals displaying evidence of or having a physiological tendency toward loss of bone mass. The metabolites specifically named in that patent, i.e., $1\alpha$-hydroxyvitamin $D_3$, $1\alpha$-hydroxyvitamin $D_2$ $1\alpha,25$-dihydroxyvitamin $D_3$,$1\alpha,25$-dihydroxyvitamin $D_2$ and $1,24,25$-trihydroxyvitamin $D_3$, although capable of the activity described and claimed in that patent are also characterized by the disadvantage of causing hypercalcemia especially if used with the conventional calcium supplement treatment. Therefore, use of these compounds to treat osteoporosis has not been widely accepted. U.S. Pat. Nos. 3,833,622 and 3,901,928 respectively suggest using the hydrate of 25-hydroxyvitamin $D_3$ and $1\alpha$-hydroxyvitamin $D_3$ for treatment of osteoporosis in a general expression of utility for those compounds. It is well known both of those compounds express traditional vitamin D-like activity, including the danger of hypercalcemia.

U.S. Pat. No. 4,588,716 also suggests the use of $1\alpha$, 25-dihydroxy-24-epi-vitamin $D_2$ to treat bone disorders characterized by the loss of bone mass, such as osteoporosis. This compound expresses some of the vitamin D-like characteristics affecting calcium metabolism such as increasing intestinal calcium transport and stimulating the mineralization of new bone. It has the advantage of minimal effectiveness in mobilizing calcium from bone. The 24-epi compound may be administered alone or in combination with a bone mobilization inducing compound such as a hormone or vitamin D compound such as $1\alpha$-hydroxyvitamin $D_3$ or $D_2$ or $1\alpha,25$-dihydroxyvitamin $D_3$ or $D_2$.

U.S. Pat. No. 5,194,431 discloses the use of 24-cyclopropane vitamin $D_2$ compounds in treating osteoporosis. Also, U.S. Pat. No. 4,851,401 discloses the use of cyclopentano 1,25-dihydroxyvitamin $D_3$ compounds in the treatment of osteoporosis and related diseases.

In an ongoing effort to develop a treatment for osteoporosis, the carbon 20 position of the side-chain was investigated to determine its potential. Altering the order of substituents or the substitution pattern on carbon 20 could result in a change of minimum energy position for conformations around the $C_{17}$–$C_{20}$ bond, and consequently, in a change of side-chain orientation with respect to the ring system. Orientation of the side-chain with respect to the ring system and configuration on the $C_{20}$ may have important consequences for biological properties of cholestane derivatives, in particular vitamin D compounds. It is well documented that binding of $1\alpha,25$-dihydroxyvitamin $D_3$ (1, Scheme 1) involves active centers in the ring A and triene system as well as in the side-chain. Altering the "normal configuration" around C₇-C₂₀ bond in vitamin D could change the distance between active centers within the molecule, and thus result in a change in activity of such compounds.

A synthesis of 1α,25-dihydroxy-21-norvitamin D₃ was described in Kuboderal et al, "Synthetic Studies of Vitamin D Analogs. X. Synthesis and Biological Activities of 1α,25-Dihydroxy-21-Norvitamin D₃", Chem. Pharm. Bull., 40(3) 648–651 (1992) from 1α-hydroxydehydroepiandrosterone. Certain biological properties of 1α,25-dihydroxy-21-norvitamin D₃ were also examined and compared with those of 1α,25-dihydroxyvitamin D₃ and 1α,25-dihydroxy-21-nor-20-oxavitamin D₃ to evaluate the effect of the 21-methyl substituent on biological properties.

SUMMARY OF THE INVENTION

The present invention provides a novel treatment of metabolic bone diseases which utilizes 21-norvitamin D compounds exhibiting a desired, and highly advantageous, pattern of biological activity. These compounds are characterized by a marked intestinal calcium transport activity, as compared to that of 1α,25-dihydroxyvitamin D₃, while exhibiting much lower activity than 1α,25-dihydroxyvitamin D₃ in their ability to mobilize calcium from bone. Hence, these compounds are highly specific in their calcemic activity. Their preferential activity on intestinal calcium transport and reduced calcium mobilizing activity in bone allows the in vivo administration of these compounds for the treatment of metabolic bone diseases where bone loss is a major concern. Because of their preferential calcemic activity, these compounds would be preferred therapeutic agents for the treatment of diseases where bone formation is desired, such as osteoporosis, osteomalacia and renal osteodystrophy.

Structurally, the key feature of the compounds having these desirable biological attributes is that they are analogs of 1,25-dihydroxyvitamin D₃ in which the methyl group normally attached to the side-chain at carbon 20 has been replaced by a hydrogen atom. Thus, the compounds of this type are characterized by the following general structure:

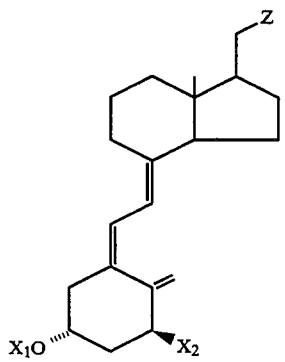

where X₁ may be hydrogen or a hydroxy-protecting group, X₂ may be hydrogen, hydroxy, or protected hydroxy, and where Z is selected from the group consisting of Y, —OY, —CH₂OY, —C≡CY and —CH=CHY, where the double bond may have the cis or trans stereochemical configuration, and where Y is selected from the group consisting of hydrogen, methyl, —CR₅O and a radical of the structure

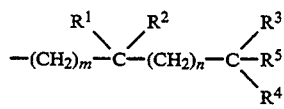

where m and n, independently, represent the integers from 0 to 5, where R¹ is selected from the group consisting of hydrogen, hydroxy, protected-hydroxy, fluoro, trifluoromethyl, and C₁₋₅-alkyl, which may be straight chain or branched and, optionally, bear a hydroxy or protected-hydroxy substituent, and where each of R², R³ and R⁴, independently, is selected from the group consisting of hydrogen, fluoro, trifluoromethyl and C₁₋₅ alkyl, which may be straight-chain or branched, and optionally bear a hydroxy or protected-hydroxy substituent, and where R¹ and R², taken together, represent an oxo group, or an alkylidene group, =CR₂R₃, or the group —(CH₂)ₚ—, where p is an integer from 2 to 5, and where R³ and R⁴, taken together, represent an oxo group, or the group —(CH₂)q—, where 9 is an integer from 2 to 5, and where R⁵ represents hydrogen, hydroxy, protected-hydroxy, or C₁₋₅ alkyl.

The present invention, therefore, provides 21-norvitamin D compounds showing preferential activity on intestinal calcium transport and reduced calcium mobilizing activity in bone, and are useful for the treatment of metabolic bone disease, such as osteoporosis, where bone loss is a major concern. More specifically, the preferred compound to be administered is 1α,25-dihydroxy-21-norvitamin D₃.

This invention also provides novel intermediate compounds formed during the synthesis of the end products. Structurally, the intermediate compounds are characterized by the following general structure:

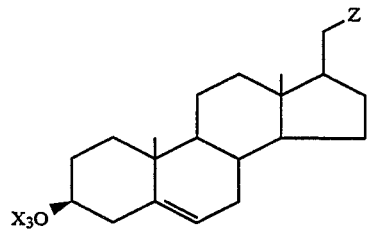

where X₃ may be hydrogen or a hydroxy-protecting group, and Z is as previously defined herein.

Other key intermediates are characterized by the following general structure:

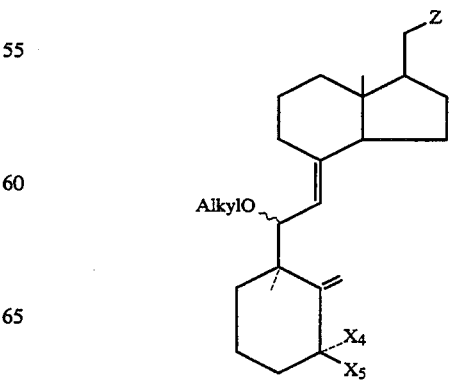

where $X_4$ and $X_5$ which may be the same or different, is hydrogen, hydroxy, or oxygen, and Z is as previously defined herein.

Still other key intermediates are 21-norvitamin $D_3$ compounds which are characterized by the following general structure:

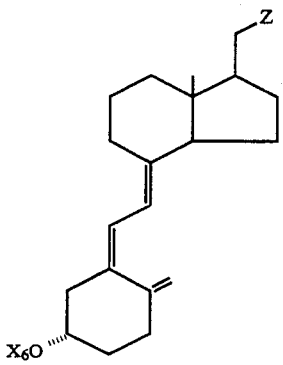

where $X_6$ may be hydrogen or a hydroxy-protecting group, and Z is as previously defined herein. In particular, 25-hydroxy-21-norvitamin $D_3$ is disclosed.

It has now been found that the loss of bone mass, which is characteristic of osteoporosis may be effectively treated by the administration of a 21-norvitamin D compound in sufficient amounts to increase bone mass. More specifically, a method of treating osteoporosis comprises the administration of an effective amount of a 21-norvitamin D compound, preferably 1α,25-dihydroxy21-norvitamin $D_3$. The above compounds may be administered alone or in combination with other pharmaceutically acceptable agents. Dosages of from not less than about 0.5 μg/day to not more than about 50 μg/day of the individual compound per se, or in combinations, are generally effective. This method has the distinct advantage that it will restore bone mass due to the insignificant bone mobilization activity of these compounds and further these compounds advantageously will not cause hypercalcemia even if the compound is administered continuously on a daily basis, as long as the appropriate compound dosages are used, it being understood that the dosage levels will be adjusted dependent on the response of the subject as monitored by methods known to those skilled in the art.

The above method, involving the administration of the indicated dosages of 21-norvitamin D compounds such as 1α,25-dihydroxy-21-norvitamin $D_3$ is effective in restoring or maintaining bone mass, and thus provides a novel method for the treatment or prevention of various forms of osteoporosis such as postmenopausal osteoporosis, senile osteoporosis and steroid-induced osteoporosis. It will be evident that the method will find ready application for the prevention or treatment of disease states other than those named, such as renal osteodystrophy.

DETAILED DESCRIPTION OF THE INVENTION

As used in the description and in the claims, the term hydroxy-protecting group signifies any group commonly used for the temporary protection of hydroxy functions, such as for example, alkoxycarbonyl, acyl, alkylsilyl, and alkoxyalkyl groups, and a protected hydroxy group is a hydroxy function derivatized by such a protecting group. Alkoxycarbonyl protecting groups are groupings such as methoxycarbonyl, ethoxycarbonyl, propoxycarbonyl, isopropoxycarbonyl, butoxycarbonyl, ixobutoxycarbonyl, tert-butoxycarbonyl, benzyloxycarbonyl or allyloxycarbonyl. The term 'acyl' signifies an alkanoyl group of 1 to 6 carbons, in all of its isomeric forms, or a carboxyalkanoyl group of 1 to 6 carbons, such as an oxalyl, amlonyl, succinyl, glutaryl group, or a aromatic acyl group such as benzoyl, or a halo, nitro or alkyl substituted benzoyl group. The word 'alkyl' as used in the description or the claims, denotes a straight-chain or branched alkyl radical of 1 to 10 carbons, in all its isomeric forms. Alkoxyalkyl protecting groups are groupings such as methoxymethyl, ethoxyethyl, methoxyethoxymethyl, or tetrahydrofuranyl and tetrahydropyranyl. Preferred alkylsilyl protecting groups are trimethylsilyl, triethylsilyl, t-butyldimethylsilyl, and analogous alkylated silyl radicals.

The vitamin D compounds useful in the present treatment are 21-norvitamin D compounds, preferably 1α,25-dihydroxy-21-norvitamin $D_3$. The above compounds may be administered alone or in combination with other pharmaceutically acceptable agents.

The 21-norvitamin D compounds or combinations thereof can be readily administered as sterile parenteral solutions by injection or intravenously, or by alimentary canal in the form of oral dosages, or transdermally, or by suppository. Doses of from about 0.5 micrograms to about 50 micrograms per day of the compounds per se, or in combination with other 1α-hydroxylated vitamin D compounds, the proportions of each of the compounds in the combination being dependent upon the particular disease state being addressed and the degree of bone mineralization and/or bone mobilization desired, are generally effective to practice the present invention. In all cases sufficient amounts of the compound should be used to restore bone mass. Amounts in excess of about 50 micrograms per day or the combination of that compound with other 1α-hydroxylated vitamin D compounds, are generally unnecessary to achieve the desired results, may result in hypercalcemia, and may not be an economically sound practice. In practice the higher doses are used where therapeutic treatment of a disease state is the desired end while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art. For example, to be effective, the 1α,25-dihydroxy-21-norvitamin $D_3$ compound is preferably administered in a dosage range of 0.5-50 μg/day. In general, either a single daily dose or divided daily dosages may be employed, as is well known in the art.

Dosage forms of the various compounds can be prepared by combining them with non-toxic pharmaceutically acceptable carriers to make either immediate release or slow release formulations, as is well known in the art. Such carriers may be either solid or liquid such as, for example, corn starch, lactose, sucrose, peanut oil, olive oil, sesame oil and propylene glycol. If a solid carrier is used the dosage form of the compounds may be tablets, capsules, powders, trochees or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

The present invention is more specifically described by the following examples, which are meant to be illustrative only of the process of synthesis and of the novel compounds, both end products and intermediates, obtainable thereby. In these examples, specific compounds identified by Arabic numerals (e.g. compounds 1, 2, 3, . . . etc.) refer to the structures so numbered in the process schematics. Additionally examples are provided which are illustrative of the distinctive biological characteristics of the new compounds, such characteristics serving as a basis for the application of these compounds in the treatment of metabolic bone disease.

Chemistry

The synthetic route to 1α,25-dihydroxy 21-norvitamin $D_3$ 2a, which includes 25-hydroxy-21-norcholesterol acetate 9a, 21-norvitamin $D_3$ 11a and 3,5-cyclo-9,10-seco-derivatives 12a, 12b as key intermediates was chosen.

For synthesis of the 5-hydroxy-21-norcholesterol 9 methodology developed for the early synthesis of 25-hydroxycholesterol was explored. Uskovic et al, *Helv. Chim. Acta,* 1974. 57:768; Wicha et al, *Synth. Comm.,* 1977, 7:215-222; and Wicha et al, *J. Chem. Soc.*, Perkin 1, 1978, 1282. Thus, readily available androstane derivative 4 was subjected to reaction with an anion generated from triethylphosphonoacetate and the condensation product 5a was transformed to the i-steroid 6a via tosylate 5b. Noteworthy, during methanolysis of tosylate 5b under Butenandt and Grosse conditions, Butenandt et al, *Chem. Ber.,* 1936, 69:2777, no exchange of the ester ethyl for methyl group occurred. Reduction of the ester group in 6a with hydride afforded allylic alcohol 6b which on hydrogenation gave the saturated derivative 7a. The respective tosylate, 7b, was coupled with lithium derivative of 3-methyl-1-butyn-3-yl 2-tetrahydropyranyl ether Barton et al, *J. Chem. Soc.,* (c), 1970, 1584, accordingly to the procedure of Uskokovic, et al, *Helv. Chim Acta,* 1973, 57:758, to give the 21-nor-23-yn cholestane derivative 8a which was hydrogenated over palladium catalyst. The product of hydrogenation, 8b, was subjected to solvolysis in glacial acetic acid to give required 25-hydroxycholesterol acetate 9b in 36% overall yield from starting 17-oxoandrostane 4 (9 steps). Alternatively, i-steroid 8b was treated with p-toluenesulphonic acid (PTSA) in aqueous dioxane to give described Pumar et al, *An. Quim.*, Ser. C, 1988, 84:105-111, 25-hydroxy-21-norcholesterol 9a which was acetylated to give 9b.

Conventional bromination-dehydrobromination of compound 9b followed by treatment of the crude product with PTSA in dioxane and chromatography on a silica gel column Uskokovic et al, *J. Org. Chem.*, 1981, 46: 1030, afforded pure acetoxy diene 10b in a 39% yield. The respective alcohol 10a was subjected to photolysis using medium-pressure UV lamp equipped with Vycor filter. The reaction was monitored with HPLC and was stopped at the ca. 50% of conversion of the starting diene. The crude product was heated in ethanol at 75° C. for 6 hours and then chromatographed to give triene 11a (at least 90% pure, accordingly to $^1$H NMR) in a 24% yield.

Homoallylic alcohol 11a was treated with tosyl chloride in pyridine to give tosylate 11b. Methanolysis, M. Sheves et al *J. Am. Chem. Soc.,* 1975, 97:6249, of tosylate 8b afforded the cyclopropane derivative 12a which was purified by chromatography. This key intermediate (12a) was hydroxylated, Paaren et al, *J. Org. Chem,* 1980, 45:3253; DeLuca et al, U.S. Pat. No. 4,555,364, to give 1α-hydroxy derivative 12b accompanied by small amount of α,β-ketone 12c which easily removed by chromatography. Solvolysis of methoxy cyclopropane 12b in acetic acid afforded acetoxy triene 2b as a mixture of 5Z and 5E isomers in a 2:1 ratio (HPLC, $^1$H NMR). Unrequired E isomer was removed by virtue of its facile reaction with maleic anhydride, DeLuca et al, U.S. Pat. No. 4,555,364. Finally, the ester group in 2b was saponified and 1α,25-dihydroxy-21-norvitamin $D_3$ 2a was purified by column chromatography.

Experimental

Melting points were determined on a Thomas Hoover capillary melting point apparatus and are uncorrected. Spectra were recorded using the following instruments: $^1$H NMR-Brucker AM 400 or AM 500, as indicated (for deuteriumchloroform solutions with tetramethylsilane as an integral standard), UV-Perkin-Elmer Lambda 3B uv/vis (for ethanol solutions), mass and high resolution mass-Kartos MS-50Ts (70 eV). All reactions involving dienes or trienes were carried out under argon. Organic solutions were dried over anhydrous sodium sulfate and solvents were evaporated on a rotary evaporator. Column chromatography was performed using silica gel, Merck, 60, 230-400 mesh and preparative layer chromatography (PLC) using precoated silica gel plates, 20×20×0.025 cm, Merck. For high pressure liquid chromatography (HPLC) Waters Associated 6VK instrument equipped with Zorbax silics column (6.2 mm×20 cm) was used.

Ethyl 6β-methoxy-3α,5-cyclo-5α-pregn-5,17(20) (E)-en-21-oate (6a)

A mixture of ethyl 3b-hydroxypregna-5,17(20) (E)-dien-21-oate (5a) (14.3 g, 0.04 mol), Wicha et al, *Synth. Comm.,* 1977, 7:215-222, tosyl chloride (9.5 g, 0.05 mol) and pyridine (50 ml) was stirred at room temperature for 4.5 hours and then it was filtered and poured into ice-cold 10% aqueous HCl (500 ml). The product was extracted with ether (3×100 ml). Usual workup of the extract afforded an oil which was crystallized from methylene chloride-hexane to give tosylate 5b m.p. 122°-124° C. (17.7 g, 86% yield).

A mixture of Tosylate 5b (17.4 g, 0.034 mol), potassium acetate (33.3 g, 0.34 mol) and anhydrous methanol (600 ml) was heated under reflux for 4 hours. Bulk of methanol was evaporated in vacuo, the residue was taken up in ether (100 ml) and water (100 ml), the layers were separated and the aqueous layer was extracted with ether (100 and 50 ml). Combined organic extracts were washed with water and then with brine. The solvent was evaporated and the residue was dried in high vacuum to give 6a (12.6 g, 100% yield).

$^1$H NMR(500) δ (ppm) 5.53(1H, t, J=2 Hz, $C_{20}$—H), 4.2-4.1(2H, m, 12 lines, OCH$_2$CH$_3$), 3.34(3H, s, OCH$_3$), 2.85-2.75(3H, m, $C_6$-and allylic H), 1.28(3H, t, J=6.6 Hz, OCH$_2$CH$_3$), 1.04(3H, s, $C_{19}$-H), 0.87(3H, s, $C_{18}$-H), 0.67(1H, dd, $J_1$=$J_2$=4.3 Hz) and 0.46(1H, dd, $J_1$=8.0, $J_2$=5.3 Hz, cyclopropane H). High resolution mass spec. for $C_{24}H_{36}O_3$ calcd.: 372.2663(M+); found: 372.2664; 357.2430(M+—CH$_3$, 24%), 341.2459(M+—CH$_3$OH, 7%) 317.2 123(M+—C$_4$H$_9$, 39%).

This product was contaminated with ca. 10% of the corresponding 3-methoxy-5-ene derivative, $^1$H NMR δ

5.38 (m, $C_{20}$-H), 3.50(m, $C_3$-H), 3.35(s. $OCH_3$) and with small mount of the starting alcohol (5a, less than 5%).

21-Hydroxy-6β-methoxy-3α,5-cyclo-5α-pregn-17,20 (E)-ene (6b)

A mixture of ester 6a (3.6 g), lithiumaluminum hydride (1.0 g) and ether (30 ml) was heated under reflux for 1 h. The reagent excess was decomposed with saturated aqueous $Na_2SO_4$ and the product was isolated in the usual way. Alcohol 6b was obtained (3.12 g, 99% yield) as colorless oil; a sample was purified by PLC (hexane-ethyl acetate, 3:2, 2 developments);

$^1$H NMR (500) δ5.27–5.20(1H, m, $C_{20}$—$\underline{H}$), 4.14(1H, dd, $J_{21a,21b}=12$, $J_{21a,20}=7$ Hz, $C_{21a}$—$\underline{H}$), 4.10(1H, dd, $J_{21b,21a}=12$, $J_{21b,20}=6$ Hz, $C_{21b}$—$\underline{H}$), 3.34(3H, s, $OC\underline{H}_3$), 2.80(1H, br s, $C_6$—$\underline{H}$), 1.05(3H, s, $C_{19}$—$\underline{H}$), 0.82(3H, s, $C_{18}$—$\underline{H}$), 0.67(1H, dd, $J_1=J_2=4.3$ Hz) and 0.45(1H, dd, $J_1=8.0$, $J_2=5.3$ Hz, cyclopropane H). High resolution mass spec. for $C_{22}H_{34}O_2$ calcd.: 330.2560($M^+$); found: 330.2595; 315.2329($M^+$—$CH_3$, 11%), 299.2382($M^+$—$CH_3OH$, 21%), 275.2012($M^+$—$C_4H_9$, 100%).

$^1$H NMR in agreement with that described. Kurek-Tyrlik et al, *J. Org. Chem.*, 1990, 55:3484.

21-Hydroxy-6β-methoxy-3α,5-cyclo-5α-pregnane (7a)

A solution of unsaturated alcohol 6b (1.94 g) in ethanol (30 ml) containing platinium oxide (0.1 g) was stirred under hydrogen for 6 h. Usual workup of the reaction mixture gave saturated alcohol 7a (1.86 g, 96% yield). A sample was purified by PLC (hexane-ethyl acetate, 4:1, 4 developments), m.p. 87°–89° C. (hexane), $^1$H NMR (500) δ 3.75–3.62(1H, m, $C_{21}$-Ha), 3.61(1H, dt, $J_{21b,21a}=10.4$. $J_{21b,20}=7.0$ Hz, $C_{21}$-Hb), 3.33(3H, s, $OC\underline{H}_3$), 2.77(1H, br s, $C_6$—$\underline{H}$), 1.03(3H, s, $C_{19}$—$\underline{H}$), 0.65(3H, s, $C_{18}$—$\underline{H}$) overlapping 0.67(1H, m, cyclopropane $\underline{H}$), 0.44(1H, dd, $J_1=7.9$, $J_2=5.2$ Hz, cyclopropane $\underline{H}$). High resolution mass spec. for $C_{22}H_{36}O_2$ calcd.: 332.2716($M^+$); found: 332.2715; 317.2469($M^+$—$CH_3$, 69%), 300.2475($M^+$—$CH_3OH$, 97%), 277.2172($M^+$—$C_4H_9$, 100%).

6β-Methoxy-21-tosyloxy-3α,5-cyclo-5α-pregnane (7b)

A procedure described for preparation of a similar compound was used. Uskokovic et al, *Helv. Chim. Acta*, 1974, 57:768.

To a stirred solution of alcohol 7a (1.71 g, 5.14 mmol) in anhydrous pyridine (2 ml) a solution of tosyl chloride (1.24 g, 6.52 mmol) in pyridine (2 ml) was added at 0° C. The mixture was stirred at 0° C. for 3 h and then a few chips of ice were added. After 5 min the mixture was poured into ice and water and the product was extracted with methylene chloride (20 and 2×15 ml). The extract was washed consecutively with 5% HCl, water, saturated aqueous $NaHCO_3$ and brine. Evaporation of the solvent gave tosylate 7b (2.43 g, 97% yield) as a crystalline mass; one recrystallization from methylene chloride-hexane gave product m.p. 110°–111° C. A sample was purified by PLC (hexane-ethyl acetate, 3:1

$^1$H NMR (500 δ 7.79(2H, d, J=8.2 Hz) and 7.35(2H, d, J=8.1 Hz, aromatic $\underline{H}$) 4.08–4.03(1H, m, $C_{21}$-Ha), 4.00(1H, dt, $J_{21b,21a}=9.6$, $J_{21b,20}=7.0$ Hz, $C_{21}$—$\underline{Hb}$), 3.32(3H, s, $OC\underline{H}_3$), 2.76(1H, br s, $C_6$—H), 2.45(3$\underline{H}$, s, $C_6H_4C\underline{H}_3$), 1.02(3H, s, $C_{19}$—$\underline{H}$), 0.65(1H, t, J=4.6 Hz, cyclopropane $\underline{H}$), 0.58(3H, s, $C_{18}$—$\underline{H}$), 0.43(1H, dd, $J_1=7.9$, $J_2=5.2$ Hz, cyclopropane H). High resolution mass spec. for $C_{29}H_{42}O_4S$ calcd.: 486.2824 ($M^+$); found: 486.2804(26%); 471.2591 ($M^+$—$CH_3$, 26%), 454.2400($M^+$—$CH_3OH$, 100%), 431.2214($M^+$—$C_4H_9$, 44%).

6β-Methoxy-25-(tetrahydropyranyl-2-oxy)-3α,5-cyclo-21-nor -5α-cholest-23-yne (8a)

To a stirred under argon solution of 3-methyl-1-butyn-3-yl 2-tetrahydropyranyl ether (2.3 g, 23.7 mmol), Barton et al *J. Chem. Soc*, (c), 1970, 1584, in anhydrous dioxane (25 ml) n-butyllithium (1.6M in hexane, 9 ml, 14.4 mmol) was added at 5° C. The mixture was stirred at 5° C. for 1.5 h and then at the room temperature for 1.5 h whereupon tosylate 7b (1.80 g, 3.7 mmol) in dioxane (20 ml) was added and the mixture was heated under reflux for 72 h. After cooling, the mixture was poured into water containing an excess of ammonium chloride and the product was extracted with ethyl acetate. The extract was washed with water and with brine. The solvent was evaporated and the residue was dried in high vacuum for 16 h to give the crude product 8a (2.98 g). A sample was purified by PLC (hexane-ethyl acetate, 4:1);

$^1$H NMR (500) δ 5.05–5.03(1H, m, THP acetal H), 3.95–3.90(1H, m) and 3.50–3.45(1H, m, THP-H), 3.33(3H, s, $OCH_3$), 2.77(1H, br s, $C_6$—H), 2.28–2.20(1H, m, 8 line, $C_{22a}$—$\underline{H}$), 2.12 and 2.13(1H, 2dt, $J_{22,22a}=16.6$, $J_{22b,20}=7.9$ Hz, $C_{22b}$—$\underline{H}$), 1.50 and 1.46(6H, 2s, $C_{26}$— and $C_{27}$—$\underline{H}$) 1.03(3H, s, $C_{19}$—$\underline{H}$), 0.64(3H, s, $C_{18}$—$\underline{H}$) overlapping 0.66–0.64(1H, m, cyclopropane H). 0.4379(1H, dd, $J_1=8$, $J_2=5.1$ Hz, cyclopropane H). High resolution mass spec. for $C_{32}H_{50}O_3$ calcd.: 482.3760($M^+$); found: 482.3755.

6β-Methoxy-25-(tetrahydropyranyl-2-oxy)-3α,5-cyclo-21-nor -5α-cholestane (8b)

A mixture of the crude product 8a (2.78 g), 5% palladium on activated carbon (0.15 g), $NaHCO_3$ (0.60 g) and dioxane (20 ml) was stirred under hydrogen for 24 h. The solid was filtered off and the filtrate was evaporated to give the saturated derivative 8b (2.98 g). A sample was purified by PLC (hexane-ethyl acetate, 4:1).

$^1$H NMR (500) δ 4.71(1H, br d, J=5.8 Hz, THP acetal H), 4.00–3.95(1H, m) and 3.50–3.45(1H, m, THP-H), 3.33(3H, s, $OCH_3$), 2.77(1H, br s, $C_6$—H), 1.20 and 1.19(6H, 2s, $C_{26}$— and $C_{27}$—H) 1.01(3H, s, $C_{19}$—H), 0.66–0.64(1H, m, cyclopropane H), 0.64(3H, s, $C_{18}$—H), 0.43(1H, dd, $J_1=8$, $J_2=5.1$ Hz, cyclopropane H). High resolution mass spec. for $C_{32}H_{54}O_3$ calcd.: 486.4073($M^+$); found: 486.4065.

25-Hydroxy-21-norcholesterol (9a)

A solution of 3,5-cyclo-derivative 8b (0.19 g) in 50% aqueous dioxane (6 ml) containing p-toluenesulphonic acid (3 mg) was stirred at 80° C. for 6 h. The mixture was diluted with water and extracted with chloroform. Usual workup of the extract afforded crude diol 9a (0.13 g) which was crystallized from methanol to give TLC pure material (0.07 g). Chromatography of the mother liquors on silica gel (3 g, hexane-ethyl acetate, 4:1) afforded additional product (0.03 g, in total 0.11 g). An analytical sample was recrystallized twice from methanol; m.p. 188°–191° C.;

$^1$H NMR (500) δ 5.38–5.36(1H, m, $C_6$—H), 3.60–3.50(1H, m, $C_3$—H), 1.21(6H, s, $C_{26}$— and $C_{27}$—H), 0.96(3H, s, $C_{19}$—H), 0.58(3H, s, $C_{18}$—H). Mass spec. m/z 388($M^+$, 100%) 370($M^+$—$H_2O$, 90%), 355(370-$CH_3$, 60%). Analysis: for $C_{26}H_{44}O_2$ calcd.:C, 80.35, H, 11.41; found: C, 80.28, H, 11.31%. Described: M.p. 188°–190° C.; $^1$H NMR in agreement with that described above, Pumar et al, *An. Quin.*, Ser. C, 1988, 84:105–111.

25-Hydroxy-21-norcholesterol 3-acetate (9b)
a. From the 6-methoxy derivative 8b A solution of crude 8b (2.98 g) in acetic acid (60 ml) was stirred at 70° C. for 2 h and then set aside for 16 h. Acetic acid was evaporated on a rotary evaporator, the residue was taken in ethyl acetate (60 ml), washed with aqueous $NaHCO_3$ and with brine. The solvent was evaporated. The residue was dissolved in chloroform, filtered through silica gel (100 g) and crystallized from acetone to give 9b (0.90 g, 56% yield from tosylate 7b), m. p. 128°–130° C.

$^1$H NMR (500) δ 5.38(1H, br d, J=5.2 Hz, $C_6$—H), 4.64–4.57(1H, m, $C_6$—H), 2.03(3H, s, $COCH_3$), 1.21(6H, s, $C_{26}$— and $C_{27}$—H), 1.03(3H, s, $C_{19}$—H), 0.58(3H, s, $C_{18}$—H). Mass spec. m/z 370($M^+$—$CH_3CO_2H$, 100%), 352(370-$H_2O$, 35%).

b. From diol 9a

A mixture of the diol (0.02 g), acetic anhydride (0.05 ml) and pyridine (0.2 ml) was set aside for 4 h. Usual workup afforded crystalline product (0.03 g) which was recrystallized from acetone to give material identical with that described under a.

3α,25-Dihydroxy-21-norcholesta-5,7-diene 3-acetate (10b)

A mixture of ene 9b (0.31 g, 0.72 mmol), powderized $NaHCO_3$ (0.31 g, 3.6 mmol), 1,3-dibromo-5,5-dimethylhydantoin 0.14 g, 0.51 mmol) and hexane (10 ml) was stirred at the reflux temperature for 30 min. After cooling, the solid was filtered off under argon and washed with hot hexane. Combined filtrates were evaporated. To the residue xylene (10 ml) and collidine (1 ml) were added, the mixture was heated under reflux for 1.5 h, cooled and poured into water. The product was extracted with ether (3×20 ml). Combined extracts were washed consecutively with cold 5% HCl (twice), water, aqueous $NaHCO_3$ and brine. Bulk of the solvent was evaporated. The residue containing the initially used xylene was diluted with toluene (50 ml) and ethanol (50 ml) and evaporated. The residue was dried in high vacuum and then it was dissolved in dioxane (10 ml) containing p-toluenesulphonic acid (10 mg). The solution was stirred at 55° C. for 4 h. The product (0.4 g) was recovered in the usual way and chromatographed on silica gel (15 g, hexane-ethyl acetate, 5:1). Fractions containing 5,7-diene were collected to give the title compound (0.12 g, 39% yield), m.p. 108°–110° C. (ether); $\lambda_{max}$ 240, 249, 260 and 272 nm;

$^1$H NMR (500) δ 5.57(1H, dd, $J_{6,7}$=5.6, $J_{6,4a}$=2.5 Hz, $C_6$—H), 5.38(1H, dt, $J_{7,6}$=5.6, $J_{7,9}$=$J_{7,14}$=2.7 Hz, $C_6$—H), 4.71(1H, tt, $J_1$=11.5, $J_2$=4.5 Hz, $C_3$—H), 2.04(3H, s, $COCH_3$), 1.21(6H, s, $C_{26}$— and $C_{27}$—H), 0.96(3H, s, $C_{19}$—H), 0.52(3H, s, $C_{18}$—H). High resolution mass spec. for $C_{28}H_{44}O_3$ calcd.: 428.3290($M^+$); found: 428.3295 (20%), 368.3052($M^+$—$H_3CO_2H$, 100%).

3β,25-Dihydroxy-21-norcholesta-5,7-diene (10b)

A solution of acetate 10a (0.12 g) in ethanol (10 ml) containing 5% aqueous NaOH (0.5 ml) was set aside for 4 h and then the solvent was evaporated in vacuo. The residue was taken in ethyl acetate (30 ml) and washed consecutively with 5% HCl, water, saturated aqueous $NaHCO_3$. Evaporation of the solvent gave alcohol 10b (0.11 g) as an amorphous solid, which was used for the next step without purification; a sample was crystallized from toluene; m.p. 195°–198° C., $\lambda_{max}$ 240, 249, 260 and 272 nm.

$^1$H NMR (500) δ 5.58(1H, dd, $J_{6,7}$=5.7, $J_{6,4a}$=2.3 Hz, $C_6$—H), 5.39(1H, dt, $J_{7,6}$=5.6, $J_{7,9}$=$J_{7,14}$=2.8 Hz, $C_6$—H), 3.70–3.60(1H, tt, $J_1$=10.8, $J_2$=4.5 Hz, $C_3$—H), 1.21(6H, s, $C_{26}$— and $C_{27}$—H), 0.95(3H, s, $C_{19}$—H), 0.52(3H, s, $C_{18}$—H). High resolution mass spec. for $C_{26}H_{42}O_2$ calcd.: 386.3185($M^+$); found: 386.3189(100%), 371.2949($M^+$—$CH_3$, 20%), 368.3032($M^+$—$H_2O$, 61%).

3α,25-Dihydroxy-21-nor-9,10-secocholesta-5Z,7E,10(19)-triene (11a)

A solution of diene 10a (0.11 g) in benzene-ether (2:8, 120 ml), cooled in ice-water bath was irradiated with Hanovia 608A36 medium-pressure UV lamp equipped with a Vycor filter. After 15 min (HPLC analysis indicated over 50% conversion) the solvent was evaporated and the residue was dissolved in ethanol (30 ml) and heated at 75° C. for 6 h. The solvent was removed and the residue was chromatographed on silica gel (12 g, hexane-ethyl acetate, 5:1) to give triene 8a (0.027 g, 24% yield) and unchanged diene 10a (0.030 g). $^1$H NMR spectrum and HPLC analysis indicated that compound 11a was over 90% pure.

$^1$H NMR (400) δ 6.23(1H, d, $J_{6,7}$=11.3 Hz, $C_6$—H), 6.03(1H, d, $J_{7,6}$=11.3 Hz, $C_7$—H), 5.04(1H, d, J=1.3 Hz, $C_{19}$-Ha), 4.81 (1H, d, J=2 Hz, $C_{19}$-Hb), 3.94(1H, tt, $J_1$=7.5, $J_2$=3.5 Hz, $C_3$—H), 1.20(6H, s, $C_{26}$— and $C_{27}$—H), 0.44(3H, s, $C_{18}$—H). High resolution mass spec. for $C_{26}H_{42}O_2$ calcd.: 386.3185($M^+$); found: 386.3182(33%), 368.3040($M^+$—$H_2O$, 6%), 353.2829($M^+$—$H_2OCH_3$, 24%).

3β,25-Dihydroxy-21-nor-9,10-secocholesta-5Z,7E,10(19)-triene 3-tosylate (11b)

A mixture of alcohol 11a (27 mg, 0.07 mmol), p-toluene-sulphonyl chloride (20 mg, 0.1 mmol) and pyridine (0.25 ml) was stirred at 5° C. for 48 h and then diluted with ethylacetate (15 ml) and washed with 2% HCl, water, aqueous $NaHCO_3$ and brine. Evaporation of solvent gave tosylate 11b (0.025 g) as an amorphous solid, which was used for the next step without purification. A sample was chromatographed on silica gel (1 g, hexane-ethyl acetate, 5:1);

$^1$H NMR (500) δ 7.80(2H, d, J=8.3 Hz) and 7.34(2H, d, J=7.8 Hz, aromatic H), 6.10(1H, d, $J_{6,7}$=11.3 Hz, $C_6$—H), 5.10(1H, d. $J_{7,6}$=11.4 Hz, $C_7$—H), 5.03(1H, d, J=1.3 Hz, $C_{19a}$—H), 4.82(1H, d, J=2 Hz, $C_{19}$—H), 4.75–4.65(1H, m, $C_3$—H), 2.45(3H, s, $C_6H_4CH_3$), 1.21(6H, s, $C_{26}$— and $C_{27}$—H), 0.43(3H, s, $C_{18}$—H); this sample was contaminated with ca. 15% of byproduct with $C_{18}$H signal at δ 0.452, which was not identified.

25-Hydroxy-6ξ-methoxy-3α, 5β-cyclo-21-nor-9,10-secocholesta-7E,10 (19)-diene (12a)

A mixture of rosylate lib (0.020 g), anhydrous methanol (25 ml) and powderized $NaHCO_3$ (0.20 g) was set aside at 37° C. for 48 h. The solid was filtered off and washed with ethyl acetate. Combined filtrates were evaporated in vacuo, the residue was dissolved in ethyl acetate (20 ml) and washed with water. The solvent was removed and the crude product was chromatographed on silica gel (4.5 g. hexane-ethyl acetate, 5:1) to give the methoxy derivative 12a (0.010 g) as a single isomer.

$^1$H NMR (500) δ 5.04(1H, br s, $C_{19}$-Ha), 4.99(1H, br d, $J_{7,6}$=9.3 Hz, $C_7$—H), 4.88(1H, br s, $C_{19}$-Hb), 4.17(1H, d, $J_{6,7}$=9.3 Hz, $C_6$—H), 3.26(3H, s, $OCH_3$), 1.21(6H, s, $C_{26}$— and $C_{27}$—H), 0.92(1H, dd, $J_1$=8.0, $J_2$=4.6 Hz, cyclopropane H), 0.74(1H, t, J=4.5, Hz, cyclopropane H), 0.43(3H, s, $C_{18}$—H). High resolution mass spec. for $C_{27}H_{44}O_2$ calcd.: 400.3341($M^+$); found: 400.3329(15%), 385.3110($M^+$—$CH_3$, 3%), 368.3066($M^+$—$CH_3OH$, 49%).

1α,25-Dihydroxy-6ξ-methoxy,3α,5β-cyclo-21-nor-9,10-secocholesta-7E,10(19)-diene (12b) and 25- hydroxy-6ξ-methoxy-1-oxo-3α,5β-cyclo-21-nor-9,10-secocholesta-7E,10(19)-diene (12c)

The described procedure for hydroxylation of cyclovitamin was used.

A mixture of selenium dioxide (Aldrich, 99.999%, 3.62 mg, 0.033 mmol), t-butylhydroperoxide (Aldrich, 3M in 2,2,4-trimethylpentane, 56 μL, 0.168 mmol) and methylene chloride (1 ml) were stirred at room temperature for 30 min and then pyridine (6 μL, 0.07 mmol) was added. After a few minutes diene 12a (5 mg) in methylene chloride (1 ml) was added. The mixture was stirred for 1 h whereupon 10% aqueous NaOH was added, stirring was continued for 10 min and the mixture was diluted with methylene chloride (10 ml). Layers were separated and the organic layer was washed with 10% NaOH and brine. Evaporation of the solvent gave a residue (7 mg) which was chromatographed on silica gel (1 g, hexane-ethyl acetate, 5:1) to give (in order of elution):

1. 1-oxo-derivative 12c (1 mg), $\lambda_{max}$=242 nm. $^1$H NMR (400) δ 6.03(1H, br s, $C_{19}$-Ha), 5.62(1H, br s, $C_{19}$-Hb) 5.02(1H, br d, $J_{7,6}$=9 Hz, $C_7$—H), 4.07(1H, d, $J_{6,7}$=9 Hz, $C_6$—H), 3.31(3H, s, $OCH_3$), 1.21(6H, s, $C_{26}$— and $C_{27}$—H), 0.95–0.85(1H, m, cyclopropane H), 0.58(1H, t, J=4.5 Hz, cyclopropane H), 0.51(3H, s, $C_{18}$—H); High resolution mass spec. for $C_{27}H_{42}O_3$ calcd.: 414.3134(M+); found: 414.3140(3%), 382.2878(M+—$CH_3OH$, 6%).

2. 1β-Hydroxy-derivative 12b (2 mg) which was used immediately for the next step; $^1$H NMR (400) δ 5.24(1H, d, J=1.5 Hz, $C_{19}$-HE), 5.16(1H, br s, $C_{19}$-HZ), 4.95(1H, d, $J_{7,6}$=9.3 Hz, $C_7$—H), 4.30–4.20(2H, d, $J_{6,7}$=9.4 Hz overlapping a multiplet, $C_6$— and $C_1$—H), 3.26(3H, s, $OCH_3$), 1.26(6H, s, $C_{26}$— and $C_{27}$—H), 0.94(1H, dd, $J_1$=4.9, $J_2$=8.1 Hz, cyclopropane H), 0.60(1H, t, J=4.5, Hz, cyclopropane H), 0.43(3H, s, $C_{18}$—H).

1α,25-Dihydroxy-21-norvitamin $D_3$1-acetate (2b) and (5E)
1α,25-Dihydroxy-21-norvitamin $D_3$1-acetate A solution of the 3,5-cyclo derivative 12b (2 mg) in acetic acid (15 ml) was stirred at 55° C. for 20 min whereupon acetic acid was evaporated in vacuo. The residue was taken in ethyl acetate (15 ml) and washed with aqueous $NaHCO_3$ and brine. After evaporation of the solvent a mixture of compounds 2b and its geometric isomer (2 mg) in a ratio ca. 2:1 (HPLC, NMR) was obtained; HLPC, 4.5% iso-propanol in hexane, retention times 12.2 and 15 min, respectively.

$^1$H NMR (400), isomer 2b, δ 6.34(1H, br d, J=11.2 Hz, $C_6$—H), 6.02(1H, d, $J_{7,6}$=11.2 Hz, $C_7$—H), 5.34(1H, br s, $C_{19}$-HE), 5.27–5.15(1H, m, $C_3$—H), 5.01(1H, br s, $C_{19}$-HZ), 4.45–4.35(1H, m, $C_1$—H), 2.03(3H, s, $CH_3CO$), 1.25 and 1.21(6H, 2s, $C_{26}$— and $C_{27}$—H), 0.9374(1H, dd, $J_1$=4.9, $J_2$=8.1 Hz, cyclopropane H), 0.44(3H, s, $C_{18}$—H); 5E isomer of 2b, 6.57(1H, d, J=11.2 Hz, $C_6$H), 5.81 (1H, d, J=11.2 Hz, $C_7$—H), 5.13(1H, br s, $C_{19a}$—H), 4.99(1H, br s, $C_{19b}$—H), 4.51–4.45(1H, br t, J=2 Hz, $C_1$—H) remaining signals over imposed with those of the 5Z isomer.

1α,25-Dihydroxy-21-norvitamin $D_3$ (2a)

The following procedure disclosed in U.S. Pat. No. 4,555,364 for separation of E and Z isomers was used.

The above described mixture of 2b and its 5E isomer was dissolved in ethyl acetate (0.5 mil) and treated with a solution of maleic anhydride (2 mg) in ethyl acetate (0.5 ml). After 4 h (HPLC indicated complete consumption of the E-isomer), the mixture was diluted with ethyl acetate (15 mil) and washed with saturated $NaHCO_3$ and brine. The solvent was evaporated and the residue 6 mg) was dissolved in ether (1 ml) and methanol (1 ml) and treated for 2.5 h (stirring) with powderized $K_2CO_3$ (50 mg). The mixture was diluted with ethyl acetate (15 ml) washed with water and evaporated to give residue (1 mg) which was chromatographed on silica gel (0.5 g, gradient elution hexane-ethyl acetate, 4:1 to hexane-ethyl acetate, 1:4) to give the title compound (1 mg) $\lambda_{max}$ 264 nm;

$^1$H NMR (400) δ 6.38(1H, br d, J=11.4 Hz, $C_6$—H), 6.01(1H, d, $J_{7,6}$=11.4 Hz, $C_7$—H), 5.32(1H, br s, $C_{19}$-$H_E$), 5.00(1H, br a, $C_{19}$-$H_z$), 4.47–4.40(1H, m, $C_1$—H), 4.27–4.20(1H, m, $C_3$—H), 1.21 (6H, s, $C_{26}$— and $C_{27}$—H), 0.44(3H, s, $C_{18}$—H). High resolution mass spec. for $C_{25}H_{42}O_3$ calcd.: 402.3134(M+—2HO, 83%), 348.2809(M+—3$H_2O$, 21%)

SCHEME 1

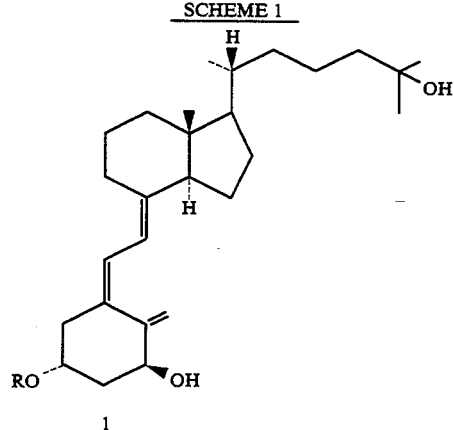

1

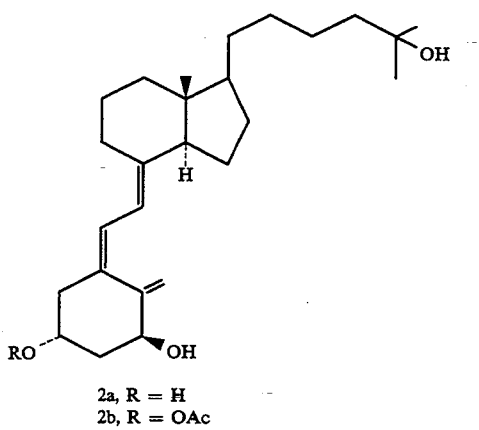

2a, R = H
2b, R = OAc

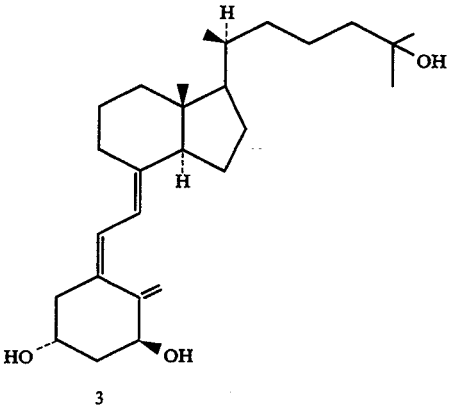

3

-continued
SCHEME 1
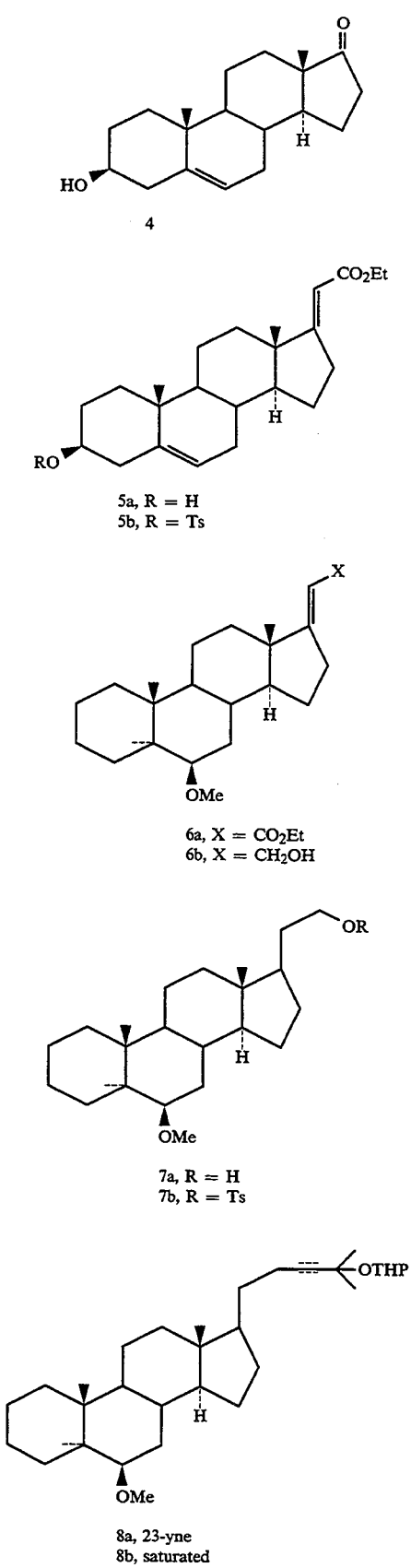
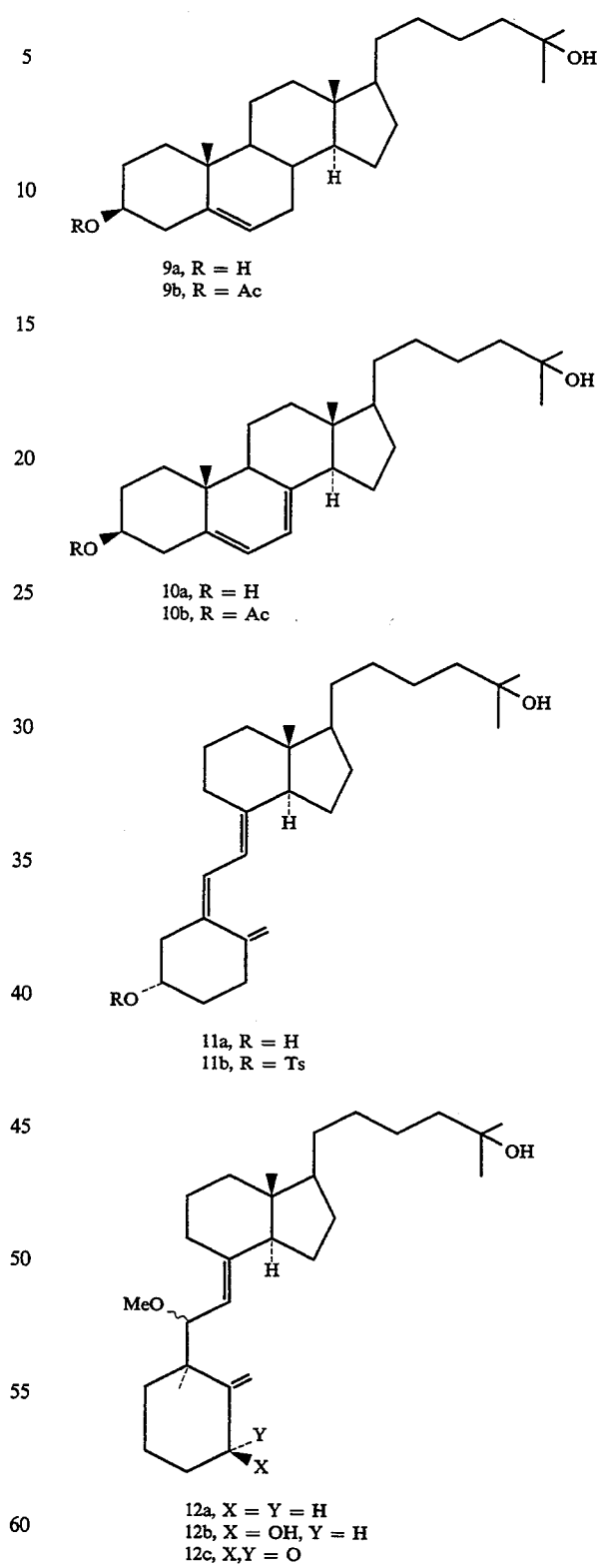
Biological Activity
Rats were maintained on a normal calcium and normal phosphorus diet for one week (0.47% Ca, 0.3% P), then switched to a —Ca diet for the duration of the experiment (0.02% Ca). Vitamin D compounds were suspended in mixtures of ethanol and propylene glycol (5%:95%) and were administered daily for 7 days peritoneally.

After 7 days the rats were killed and the duodena were used for determination of intestinal calcium transport by the everted intestinal sac technique (Martin & DeLuca, 1967) and serum calcium (bone calcium mobilization). The tests were made against 1,25-dihydroxyvitamin $D_3$ and are reported in Table 1.

TABLE 1

INTESTINAL CALCIUM TRANSPORT AND BONE CALCIUM MOBILIZING ACTIVITIES OF 21-NOR-1α,25-DIHYDROXYVITAMIN $D_3$

| Compound | Amount (μg/day/7 day) | S/M (Mean ± SEM) | Serum Ca (Means ± SEM) |
|---|---|---|---|
| -D | 0 | 4.1 ± 0.44 | 4.1 ± 0.23 |
| 1.25-(OH)$_2$D$_3$ | 1.0 | 7.9 ± 0.33 | 5.3 ± 0.10 |
| 21-nor-1,25-(OH)$_2$D$_3$ | 0.1 | 7.9 ± 0.82 | 4.5 ± 0.1 |
|  | 1.0 | 8.0 ± 0.65 | 4.5 ± .09 |

The results show that the 21-nor-1,25-dihydroxyvitamin D compound is less active than 1,25-dihydroxyvitamin $D_3$ in both mobilization of calcium from bone and intestinal calcium transport. However, the 21-nor-1,25-dihydroxyvitamin $D_3$ compound has highly significant intestinal calcium transport activity. The amount of bone calcium mobilizing activity is considerably less than 1,25-dihydroxyvitamin $D_3$. These compounds therefore, by showing preferential activity on intestinal calcium transport and reduced calcium mobilizing activity in bone suggest that they are preferred agents for the treatment of a disease where bone loss is a major issue, such as osteoporosis, osteomalacia and renal osteodystrophy.

For treatment purposes, the novel compounds of this invention may be formulated for pharmaceutical applications as a solution in innocuous solvents, or as an emulsion, suspension or dispersion in suitable solvents or carriers, or as pills, tablets or capsules together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, parenterally or transdermally. The compounds are advantageously administered by injection or by intravenous infusion of suitable sterile solutions, or in the form of liquid or solid doses via the alimentary canal, or in the form of creams, ointments, patches, or similar vehicles suitable for transdermal applications. Doses of from 0.5 μg to 50 μg per day of the compounds are appropriate for treatment purposes, such doses being adjusted according to the disease to be treated, its severity and the response of the subject, as is well understood in the art. Since the new compounds exhibit specificity of action, each may be suitably administered alone, in situations where only calcium transport stimulation is desired, or together with graded doses of another active vitamin D compound—e.g. 1α-hydroxyvitamin $D_2$ or $D_3$, or 1α,25-dihydroxyvitamin $D_3$—in situations where some degree of bone mineral mobilization (together with calcium transport stimulation) is found to be advantageous.

We claim:

1. A compound having the formula

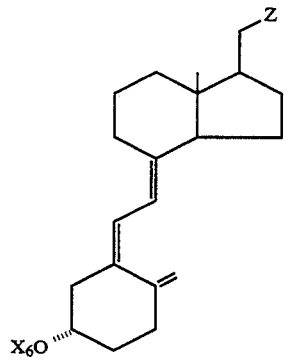

where $X_6$ may be hydrogen or a hydroxy-protecting group, and Z is selected from the group consisting of Y, —OY, —CH$_2$OY, —C≡CY and —C=CHY, where the double bond may have the cis or trans stereochemical configuration, and where Y is selected from the group consisting of hydrogen, methyl, —CR$^5$O and a radical of the structure,

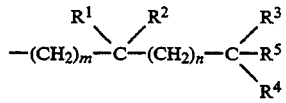

where m and n independently represent integers from 0 to 5, where $R^1$ is selected from the group consisting of hydrogen, hydroxy, protected-hydroxy, fluoro, trifluoromethyl, and C$_{1-5}$ alkyl, which may be straight-chain or branched and optionally bear a hydroxy or protected-hydroxy substituent, and where each of $R^2$, $R^3$, and $R^4$ independently is selected from the group consisting of hydrogen, fluoro, trifluoromethyl, and $C_{1-5}$ alkyl, which may be straight-chain or branched and optionally bear a hydroxy or protected-hydroxy substituent, and where $R^1$ and $R^2$, taken together, represent an oxo group, or an alkylidene group, $=CR^2R^3$ or the group $-(CH_2)p-$, where p is an integer from 2 to 5, and where $R^3$ and $R^4$, taken together, represent an oxo group, or the group $-(CH_2)q$, where q is an integer from 2 to 5, and where $R^5$ represents hydrogen, hydroxy, protected hydroxy, or $C_{1-5}$ alkyl.

2. The compound of claim 1 where Z is $CH_2CH_2CH_2C(CH_3)_2OH$ and $X_6$ is hydrogen.

3. A pharmaceutical composition containing at least one compound as claimed in claim 1 together with a pharmaceutically acceptable excipient.

4. The pharmaceutical composition of claim 3 containing 21-nor-1α,25-dihydroxyvitamin $D_3$ in an amount from about 0.5 μg to about 50 μg.

5. A compound having the formula

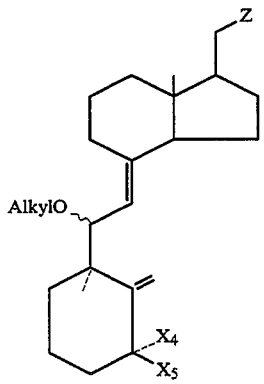

where $X_4$ and $X_5$, which may be the same or different are hydrogen, hydroxy, or taken together to form an oxo group, and Z is as defined in claim 1.

* * * * *

UNITED STATES PATENT AND TRADEMARK OFFICE
CERTIFICATE OF CORRECTION

PATENT NO. : 5,384,313
DATED : January 24, 1995
INVENTOR(S) : Hector F. DeLuca et al It is certified that error appears in the above-indentified patent and that said Letters Patent is hereby corrected as shown below:

| | |
|---|---|
| Col. 4, line 22: | Delete "9" and substitute therefor ---q---. |
| Col. 7, line 21: | Delete "9a" and substitute therefor ---9b---. |
| Col. 8, line 2: | Delete "8b" and substitute therefore ---11b---. |

IN THE CLAIMS:

| | |
|---|---|
| Col. 18, line 45 | Delete "-C=CY" and substitute therefore --- -C≡CY ---. |
| Col. 19, line 5: | After "=CR$^2$R$^3$" insert --- , ---. |

UNITED STATES PATENT AND TRADEMARK OFFICE
CERTIFICATE OF CORRECTION

PATENT NO. : 5,384,313

DATED : January 24, 1995

INVENTOR(S) : Hector F. DeLuca et al

It is certified that error appears in the above-indentified patent and that said Letters Patent is hereby corrected as shown below:

Col. 20, line 17, after "together" delete "to" and substitute therefor —,—.

Signed and Sealed this

Nineteenth Day of March, 1996

Attest:

BRUCE LEHMAN

*Attesting Officer*     *Commissioner of Patents and Trademarks*